(12) United States Patent
Yang

(10) Patent No.: US 10,295,379 B2
(45) Date of Patent: May 21, 2019

(54) OPTICAL FIBER SENSING LAYER AND MONITORING SYSTEM USING THE SAME

(71) Applicant: HUIJIA HEALTH LIFE TECHNOLOGY CO., LTD., Zhubei, Taiwan (CN)

(72) Inventor: Shuchen Yang, Zhubei (CN)

(73) Assignee: HUIJIA HEALTH LIFE TECHNOLOGY CO., LTD., Zhubei, Taiwan (CN)

( * ) Notice: Subject to any disclaimer, the term of this patent is extended or adjusted under 35 U.S.C. 154(b) by 54 days.

(21) Appl. No.: 15/034,804

(22) PCT Filed: Jan. 26, 2015

(86) PCT No.: PCT/CN2015/071558
§ 371 (c)(1),
(2) Date: May 5, 2016

(87) PCT Pub. No.: WO2016/095324
PCT Pub. Date: Jun. 23, 2016

(65) Prior Publication Data
US 2016/0349085 A1 Dec. 1, 2016

(30) Foreign Application Priority Data
Dec. 15, 2014 (CN) .......................... 2014 1 0775644

(51) Int. Cl.
*A61B 5/00* (2006.01)
*A61B 5/11* (2006.01)
(Continued)

(52) U.S. Cl.
CPC ........... *G01D 5/353* (2013.01); *A61B 5/0059* (2013.01); *A61B 5/0205* (2013.01);
(Continued)

(58) Field of Classification Search
CPC .... G01D 5/353; A61B 5/0059; A61B 5/0205; A61B 5/02055; A61B 5/0873;
(Continued)

(56) References Cited

U.S. PATENT DOCUMENTS 5,134,281 A * 7/1992 Bryenton ............. A61B 5/1073
250/227.14
5,193,129 A * 3/1993 Kramer ................... G01L 1/245
250/227.14
(Continued)

FOREIGN PATENT DOCUMENTS

CN 2106554 6/1992
CN 2284555 6/1998
(Continued)

*Primary Examiner* — Christopher A Flory
(74) *Attorney, Agent, or Firm* — Hamre, Schumann, Mueller & Larson, P.C.

(57) ABSTRACT

An optical fiber sensing layer that includes two layers of pressure-sensitive assembly films which are vertically superposed and at least one layer of flexible and smooth film that separates a space between the two layers of pressure-sensitive assembly film into at least two interlayers. Each interlayer is provided with at least one optical fiber row which has many S-shaped concatenated cablings and extends along a first direction. The cablings of the vertically adjacent optical fiber rows are staggered and superposed. The optical fiber rows are uniformly distributed on the pressure-sensitive assembly films to form optical fiber sensing areas, and the bending portions of the cablings of two vertically adjacent optical fiber rows are staggered and superposed.

20 Claims, 9 Drawing Sheets

(51) Int. Cl.
*G01L 1/24* (2006.01)
*A61B 5/087* (2006.01)
*G01D 5/353* (2006.01)
*A61B 5/0205* (2006.01)

(52) U.S. Cl.
CPC ........ *A61B 5/02055* (2013.01); *A61B 5/0873* (2013.01); *G01D 5/35374* (2013.01); *G01L 1/242* (2013.01); *A61B 5/1102* (2013.01); *A61B 5/6804* (2013.01); *A61B 5/6891* (2013.01); *A61B 5/6892* (2013.01); *A61B 2562/029* (2013.01); *A61B 2562/0247* (2013.01); *A61B 2562/0266* (2013.01); *A61B 2562/0271* (2013.01)

(58) Field of Classification Search
CPC ... A61B 5/1102; A61B 5/6804; A61B 5/6891; A61B 5/6892
USPC .......................................................... 600/476
See application file for complete search history.

(56) References Cited

U.S. PATENT DOCUMENTS

| | | | | |
|---|---|---|---|---|
| 5,212,379 | A * | 5/1993 | Nafarrate | A61B 5/113 250/227.14 |
| 5,241,300 | A * | 8/1993 | Buschmann | A61B 5/1135 340/531 |
| 5,291,013 | A * | 3/1994 | Nafarrate | A61B 5/113 128/925 |
| 5,293,039 | A * | 3/1994 | Mongiols | G08B 13/10 250/227.14 |
| 5,357,813 | A * | 10/1994 | Weinberger | G01L 1/245 73/800 |
| 5,868,677 | A | 2/1999 | Iwanaga et al. | |
| 6,498,652 | B1 * | 12/2002 | Varshneya | A61B 5/113 356/477 |
| 6,607,486 | B1 * | 8/2003 | Watson | A61B 5/0011 250/227.14 |
| 6,816,266 | B2 * | 11/2004 | Varshneya | A61B 5/113 356/477 |
| 7,747,386 | B2 * | 6/2010 | Hishida | B60R 21/0136 250/227.14 |
| 9,186,078 | B2 * | 11/2015 | Sohma | G02B 6/02033 |
| 9,360,351 | B2 * | 6/2016 | Van Thienen | G01D 11/30 |
| 9,420,964 | B2 * | 8/2016 | Mitachi | A61B 5/113 |
| 9,572,517 | B2 * | 2/2017 | Ng | A47D 15/003 |
| 2003/0095263 | A1 * | 5/2003 | Varshneya | A61B 5/113 356/477 |
| 2005/0107870 | A1 * | 5/2005 | Wang | A61L 31/10 623/1.44 |
| 2007/0010702 | A1 * | 1/2007 | Wang | A61F 2/82 600/8 |
| 2008/0047364 | A1 * | 2/2008 | Yoshida | G01L 1/24 73/862.51 |
| 2008/0221488 | A1 | 9/2008 | Kurono et al. | |
| 2010/0049010 | A1 * | 2/2010 | Goldreich | A61B 5/0002 600/301 |
| 2010/0279125 | A1 * | 11/2010 | Buyuktanir | B29C 39/20 428/432 |
| 2011/0085759 | A1 * | 4/2011 | Lee | G01N 21/7703 385/12 |
| 2012/0203117 | A1 * | 8/2012 | Chen | A61B 5/1102 600/484 |
| 2013/0109931 | A1 * | 5/2013 | Ng | A47D 15/003 600/301 |
| 2014/0163664 | A1 * | 6/2014 | Goldsmith | A61B 17/00491 623/1.11 |
| 2014/0270669 | A1 * | 9/2014 | Sohma | G02B 6/02033 385/123 |
| 2014/0298586 | A1 * | 10/2014 | Van Thienen | G01D 5/353 5/500 |
| 2015/0309535 | A1 * | 10/2015 | Connor | G06F 1/163 361/679.03 |
| 2016/0015271 | A1 * | 1/2016 | Wang | A61B 5/0053 600/578 |
| 2016/0324431 | A1 * | 11/2016 | Ng | A61B 5/0816 |

FOREIGN PATENT DOCUMENTS

| | | |
|---|---|---|
| CN | 203970366 | 12/2014 |
| CN | 204351804 | 5/2015 |
| JP | 2005099642 | 4/2005 |
| JP | 2006343195 | 12/2006 |

\* cited by examiner

US 10,295,379 B2

OPTICAL FIBER SENSING LAYER AND MONITORING SYSTEM USING THE SAME

CROSS REFERENCE TO RELATED APPLICATIONS

This application is a US national-phase application of PCT/CN2015/071558, filed on Jan. 26, 2015. The contents of PCT/CN2015/071558 are all hereby incorporated by reference.

TECHNICAL FIELD

The application relates to the technical field of optical fiber sensing layer, especially relates to an optical fiber sensing layer and a monitoring system using the same.

BACKGROUND

Recently, with the development of the optical fiber sensing layer detecting technology, optical fiber sensing layers can be used to detected men's breaths, heartbeats, sleeps, etc., and has been gradually used into the field of house field, for example, baby cushions, seat cushions, etc.

For example, in a human breathing detecting mattress which has an optical fiber sensing layer, the appearance of mattress is a kit, the kit has an optical fiber sensing layer. The optical fiber sensing fiber includes an optical fiber and upper and lower layers of grids. The material of the grids is layer mesh material which is harder than the optical fiber. The optical fibers are arranged to be parallel with each other in the grid so as to form a sensing area. In this way, when a person lies on the mattress, as the person breathes, the upper and lower grid will be urged to press on the optical fiber and make the optical fibers deform differently. Luminance decays will happen when the optical fiber are bent, then the luminance decay values will be transmitted to an electronic assembly, through the mathematical calculation by the electronic assembly, related data about human breaths will be obtained.

However, because the optical fibers have the defects of being easy to be crushed or damaged, the upper and lower grids may prone to crush the optical fiber. During the arrangement of the optical fibers, the interval between adjacent optical fibers cannot be too small. Because of the limitation of the curvature characteristics of the optical fibers, normally the interval is at least 20 mm. If the interval is too small, the optical fiber may be broken; if the interval is too big, the deformation of the optical fiber may be unobvious when some areas of the grid are pressed, then the luminance decays will be affected. Thus, sensing blind areas may exist, which may lead to a non-uniform sensitivity of the optical fiber sensing layer and a big drop value. Besides, it further has these problems: when the same pressure acts on different sensing points of the same grid, there may be great differences between the sensitivities of different sensing points. In this way, it may cause that the breathing variation may not be detected and the upper and lower grids cannot be bent when a human body changes a posture on the sensing layer. If the grid bends, it is difficult for the optical fibers between the upper grid and the lower grids to detect the pressure from the sensing layer. Thus, the sensitivity of the optical fiber sensing layer may be decreased. Further, the thickness of the upper and lower grids must have certain thicknesses so as to make the optical fiber bend, the thicknesses cannot be adjusted according to various applications, and thus the application of the sensing layer is limited.

SUMMARY

A purpose of the application is to provide an optical fiber sensing layer, it aims to solve the problems in an existing optical fiber sensing layer that the optical fiber sensing layer has sensing blind areas, the sensing resolution is inconsistent, the sensing sensitivity is non-uniform, and the applied range is quite small.

The application is realized in the following way. The application provides an optical sensing fiber, which comprises two layers of pressure-sensitive assembly films which are vertically superposed and flexible, and at least one layer of flexible and smooth film which vertically separates a space between the two layers of pressure-sensitive assembly films into at least two interlayers, each interlayer is provided with at least one optical fiber row which extends along a first direction and has several S-shaped concatenated cablings, a bending portion of each cabling of the optical fiber row between the two vertically adjacent interlayers staggers and superposes.

Further, the number of the optical fiber rows on each interlayer is at least two, each of the optical fiber rows are arranged to be parallel along a second direction perpendicular to the first direction, and two adjacent optical fiber rows are end to end.

Further, the diameters of the bending portions of the cablings of the same optical fiber row on the same interlayer are equal, the diameters of the bending portions of the cablings of different optical fiber rows on the same interlayer increase or decrease gradually along the second direction.

Or further, the diameters of the bending portions of the cablings of all the optical fiber rows on the same interlayer are equal.

Or further, the diameters of the bending portions of the cablings of the same optical fiber row on the same interlayer are unequal, and two adjacent optical fiber rows are centro-symmetrical.

Further, the diameters of the bending portions of the cablings of the same optical fiber row on the same interlayer increases or decreases gradually along the first direction.

Further, patterns formed by the cablings of all the optical fiber rows on each interlayer are consistent, and the bending portions of the cablings of each optical fiber row on two adjacent interlayers stagger the same distance along the first direction.

Or further, the cablings of the optical fiber rows on two adjacent interlayers are arranged to stagger transversely and longitudinally.

The optical fiber sensing provided by the present application has the following advantages compared with the prior art.

The aforesaid optical fiber sensing layer comprises two layers of pressure-sensitive assembly films, and separates a space between the two layers of the pressure-sensitive assembly films into at least two interlayers vertically through at least one layer of flexible and smooth film. Each interlayer is provided with at least one optical fiber row, each optical fiber row has S-shape concatenated cablings. Therefore, the optical fiber row of every interlayer distributes on the pressure-sensitive assembly film along transverse and longitudinal directions uniformly and densely, thereby forming a uniform and dense optical fiber sensing area; the bending portions of the cablings of each optical fiber row between two upper and lower adjacent interlayers stagger and superpose, so that the optical fiber sensing area formed on every interlayer will stagger vertically. In this way, the sensing blind areas caused by the existing defects of the optical fiber row will be complementarily sensed by the optical fiber sensing areas of other interlayers. As long as the pressure-sensitive assembly film of the optical fiber sensing area is compressed slightly, the compression will be responded by the deformation of the optical fiber rows of the optical fiber sensing area. Moreover, when the same pressure acts on different sensing points or surfaces of the same optical fiber sensing area, the sensitivity of the optical fiber layer and the uniformity of the of the integral sensitivity of the sensing layer can be improved because the density of the optical fiber row is high, the stress is uniform, the luminance decay drop of the optical fiber is uniform and the luminance decay value is consistent. Therefore, compared with the prior art, the aforesaid optical fiber sensing layer is provided with multilayer-arranged flexible and smooth films, which change the characteristics that an optical fiber is brittle and has to deform in a grid form. Because the highly dense optical fibers are provided, the compression on the pressure-sensitive assembly film can be sensed quickly and precisely. The optical fiber sensing layer has the characteristics that the sensitivity is uniform, the luminance decay is consistent relatively, the sensitivity is high and can be adjusted, the resolution is high, and the applied range is wide. Besides, the above said optical fiber sensing layer has the characteristics of thinness, miniaturization, and great ability of electromagnetic interference resistance.

Another purpose of the application is to provide a monitoring system, comprising the aforesaid optical fiber sensing layer, an illuminant configured to provide light to the optical fiber sensing layer, an light detecting assembly configured to detect the luminance decay signal transmitted from the optical fiber sensing layer, a processing circuit configured to transform the luminance decay signal transmitted from the light detecting assembly into data representing human physiological activities, and an interface electrically connected with the processing circuit and configured to transmit the data to a user terminal.

The monitoring system provided by the application has the following advantages compared with the prior art.

Since the optical fiber sensing layer is adopted in the aforesaid monitoring system, the optical fiber sensing layer can sense the compression on the sensing film quickly and precisely, capture the changes of the luminance decay signal more sensitively and precisely, and transmit the variation of the luminance decay signal to the processing circuit. Afterwards, the variation of the luminance decay signal is transmitted to the processing circuit by the light detecting assembly. The processing circuit transforms the luminance decay signal into data representing human physiological activities in time. Finally, the processing circuit communicates with a mobile terminal or a computer terminal through a USB interface, a storage card interface or a router interface to output the data representing the human physiological activities. For example, if the data is transmitted to a cellphone, the user can monitor his/her physiological activities data conveniently and momentarily. If the data is transmitted to a computer, the management system in the computer can batch and monitor a large amount of users' physiological activities data. All in all, the aforesaid monitoring system can detect human's and animal's physiological activities such as breaths, heartbeats, sleeps, temperatures, etc., and moisture quickly and precisely. The monitoring system has characteristics of a high and adjustable sensitivity, a high resolution, an electromagnetic interference resistance, and a uniform sensitivity.

DETAILED DESCRIPTION OF THE PREFERRED EMBODIMENTS

In order to clearly describe the purposes, technical solutions and advantages of the present application, the application will be further specifically described below with reference to the accompany drawings and embodiments. It should be understood that the embodiments described herein are merely specific embodiments for explaining the present application but not intend to limit the present application.

As shown in FIGS. 1-12, the preferred embodiments are provided by the application.

It should be noted that, when a part is referred to as "fixed" or "arranged" on another part, it could be on another part directly or there may be intermediate parts between the part and the another part. When a part is referred to as "connected" with another part, it could be connected with another part directly or there may be intermediate parts between the part and the another part.

It should be noted that the position terms left, right, up and down or the like in the embodiment may merely be relative concepts or references to the normal working condition of the product, but not intended to limit the application.

Figure 1:
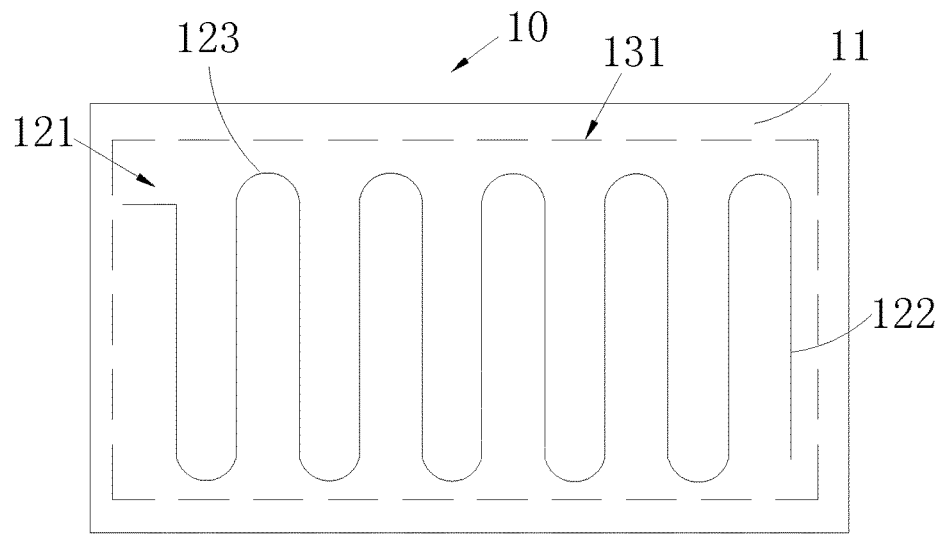
FIG. 1 is a top view of an optical fiber sensing layer provided by an embodiment of the application.
Figure 2:
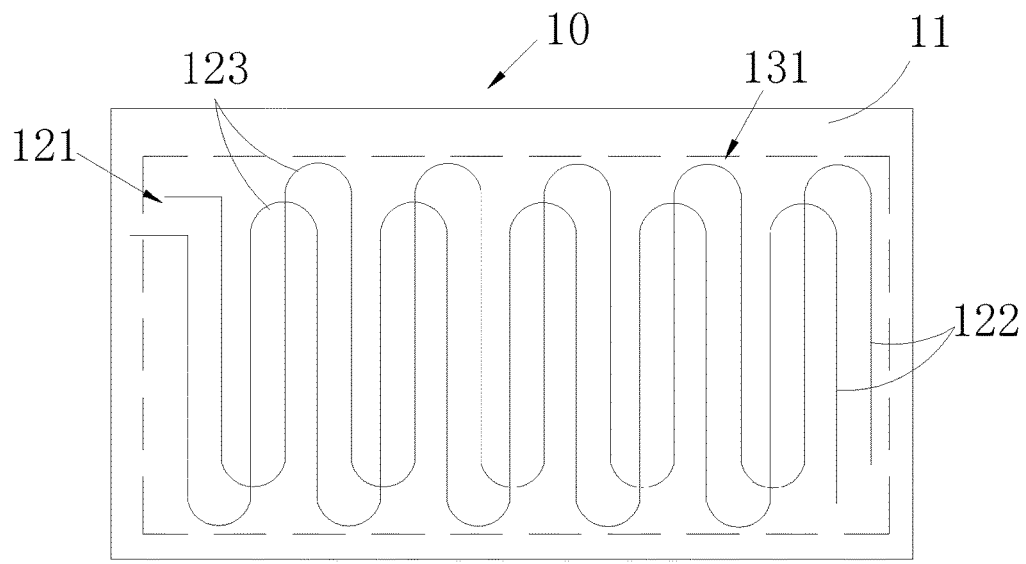
FIG. 2 is a top view of a first embodiment of the arrangement of the cablings of the optical fiber rows on every interlayer of the optical fiber sensing layer provided by the embodiment of the application.

As shown in FIG. 1, an optical fiber sensing layer 10 provided by an embodiment can be used to detect human's and animal's physiological activities such as breaths, heartbeats, sleeps, temperatures, etc., and moisture. It has been gradually applied into the field of household items, such as mattresses, pillows, insoles, seat cushions, sofas, clothes and intelligent floors, etc.

Figure 3:
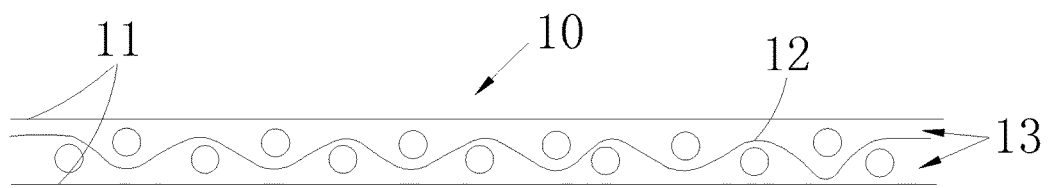
FIG. 3 is a cutaway view of the optical fiber sensing layer provided by FIG. 2.

As shown in FIG. 1 and FIG. 3, the optical fiber sensing layer 10 comprises two layers of pressure-sensitive assembly films 11 which are vertically superposed and flexible, and at least one layer of flexible and smooth film 12; the flexible and smooth film 12 vertically separates a space between the two layers of pressure-sensitive assembly film into at least two interlayers 13, each interlayer 13 is provided with at least one optical fiber row 122 which extends along a first direction and has several S-shape concatenated cablings 121, bending portions 123 of the cablings 121 of the optical fiber rows 122 between every two vertically adjacent interlayers 13 stagger and superpose.

It should be noted that the material of the pressure-sensitive assembly film 11 is flexible material. Preferably, the flexible material is silica gel or textile fabric. When the pressure-sensitive assembly film 11 is compressed, it can deform, and can also separate the optical fiber rows 122 on different interlayers 13 and ensure that the reference optical signal will not be interrupted when the original light source is not compressed. Moreover, the pressure-sensitive assembly film 11 can be a polyethylene film. This kind of pressure-sensitive assembly film 11 can not only act on a flexible protection, but also have moisture resistance, small moisture permeability, and even ensure the aridity of the optical fiber row 122.

It should be understood that, as shown in FIG. 1, because the luminance decay signal will be generated when the optical fiber row deforms axially, the area on the pressure-sensitive assembly film 11 where the optical fiber row 122 is arranged will form an optical fiber sensing area 131. Therefore, the mechanical deformation of the optical fiber row 122 of the optical fiber sensing area 131 and the pressure-sensitive assembly film 11 can be reflected by measuring the luminance decay signal generated by the optical fiber row 122.

Importantly, because the interlayer 13 is formed by separating the space between the two upper and lower pressure-sensitive assembly films 11 through at least one layer of flexible and smooth film 12, there are various structural types of the whole optical fiber sensing layer 10. For example, if there is one layer of flexible and smooth film 12, there will be two layers of interlayers 13; if there are two layers of flexible and smooth films, there will be three layers of interlayers, and so on. The number of the optical fiber row 122 of every interlayer 13 is at least one. Therefore, every optical fiber row 122 of the same interlayer 13 can be connected to an illuminant independently. The luminance decay signal of every optical fiber row 122 can be used to reflect a certain parameter, such as one of the breath, heartbeat, sleep, temperature and moisture. Alternatively, one optical fiber row 122 on the same interlayer 13 can be used to reflect two or more than two parameters. For example, one optical fiber row 122 can be used to reflect breath, heartbeat and sleep, and another one optical fiber row 122 can be used to reflect temperature and moisture. Alternatively, optical fiber rows 122 on different interlayers 13 can be used to reflect different parameters. For example, one interlayer 13 can be used to reflect sleep and another one can be used to reflect breath. Alternatively, one interlayer 13 can be used to reflect breath, heartbeat and sleep, and another one can be used to reflect temperature, etc. In this way, it makes the application combination of the above optical fiber sensing layer 10 be more abundant and more widely used.

The working principle of the optical fiber sensing layer 10 is as follows.

As shown in FIG. 1, when the above optical fiber sensing layer 10 is applied in a mattress, a pillow, a clothes, a insole, a seat cushion, a sofa, a carpet, a floor, etc., of the above optical fiber sensing layer 10 is used by a human or an animal, his/her/its physiological activities such as the breath and heartbeat can lead to sliding or vibrations and mechanical deformations of both the optical fiber row 122 and the pressure-sensitive assembly film 11, therefore the variation of the luminance decay signal will be increased. Different force magnitudes, even slight vibrations, can still be used to identify different physiological activity modes clearly. Therefore, the resolution is high. In practical applications, the variation of the luminance decay signal is input to an optical processing circuit at first, then the variation of the luminance decay signal is transformed into an electric signal computing unit, and finally the electric signal computing unit is input to a processor. Through calculation by the processor, the physiological activity signals of a human body can be achieved.

The optical fiber sensing layer 10 provided by the embodiment has the following advantages compared with the prior art.

As shown in FIG. 1 and FIG. 3, The aforesaid optical fiber sensing layer comprises two layers of pressure-sensitive assembly films, and separates a space between the two layers of the pressure-sensitive assembly films into at least two interlayers vertically through at least one layer of flexible and smooth film. Each interlayer is provided with at least one optical fiber row, each optical fiber row has S-shape concatenated cablings. Therefore, the optical fiber row of every interlayer distributes on the pressure-sensitive assembly film along transverse and longitudinal directions uniformly and densely, thereby forming a uniform and dense optical fiber sensing area; the bending portions of the cablings of each optical fiber row between two upper and lower adjacent interlayers stagger and superpose, so that the optical fiber sensing area formed on every interlayer will stagger vertically. In this way, the sensing blind areas caused by the existing defects of the optical fiber row will be complementarily sensed by the optical fiber sensing areas of other interlayers. As long as the pressure-sensitive assembly film of the optical fiber sensing area is compressed slightly, the compression will be responded by the deformation of the optical fiber rows of the optical fiber sensing area. Moreover, when the same pressure acts on different sensing points or surfaces of the same optical fiber sensing area, the sensitivity of the optical fiber layer and the uniformity of the of the integral sensitivity of the sensing layer can be improved because the density of the optical fiber row is high, the stress is uniform, the luminance decay drop of the optical fiber is uniform and the luminance decay value is consistent. Therefore, compared with the prior art, the aforesaid optical fiber sensing layer is provided with multilayer-arranged flexible and smooth films, which change the characteristics that an optical fiber is brittle and has to deform in a grid form. Because the highly dense optical fibers are provided, the compression on the pressure-sensitive assembly film can be sensed quickly and precisely. The optical fiber sensing layer has the characteristics that the sensitivity is uniform, the luminance decay is consistent relatively, the sensitivity is high and can be adjusted, the resolution is high, and the applied range is wide. Besides, the above said optical fiber sensing layer has the characteristics of thinness, miniaturization, and great ability of electromagnetic interference resistance.

It should be noted that, the minimum bending radius of a conventional optical fiber row is usually 5 mm. Therefore, a diameter of the cabling of the optical fiber sensing layer 10 provided by the embodiment is at least 10 mm.

Preferably, as shown in FIG. 1 and FIG. 3, the radian of the bending portion 123 of the cabling 121 of the optical fiber row 122 is 180°. In this way, it helps the paths of the optical fiber rows 122 on both sides of the bending portion 123 remain parallel. It further helps the circuit of the optical fiber row 122 be distributed regularly, uniformly and densely on the pressure-sensitive assembly film 11. The number of the optical fiber row 122 on the same interlayer 13 is at least two, each of the optical fiber row 122 is arranged to be parallel along a second direction perpendicular to the first direction, and every two adjacent optical fiber rows 122 are end to end. Because each optical fiber row 122 needs to be supported by an illuminant, and two adjacent optical fiber rows 122 on the same interlayer 13 are end to end, in this way, the number of the optical fiber link of the same interlayer 13 is one, and it only needs to be supported by one illuminant. Several optical fiber rows 122 are wriggled and twined in the first direction, that is, the shape of the several optical fiber rows 122 appears to be horizontally S-shaped. In the second direction, the several optical fiber rows 122 appear to be parallel-arranged longitudinally. Arranging the cabling 121 of the optical fiber row 122 horizontally and longitudinally makes the wiring of the optical fiber rows 122 on the pressure-sensitive assembly film 11 be more regular, more uniform and denser, so that the optical fiber sensing area 131 on the pressure-sensitive assembly film 11 can sense the compression on the pressure-sensitive assembly film 11 more sensitively, thus the variation of the luminance decay signal can be captured more sensitively and precisely. Therefore, the sensitivity of the aforesaid optical fiber sensing layer 10 is uniform, the luminance decay value of the aforesaid optical fiber sensing layer is relative consistent, the sensitivity of the aforesaid optical fiber sensing layer is high and can be adjusted, and the resolution of the aforesaid optical fiber sensing layer is high.

The following embodiment is a first embodiment of the diameter arrangement of the bending portion 123 of the cabling 121 of the optical fiber row 122.

Figure 4:
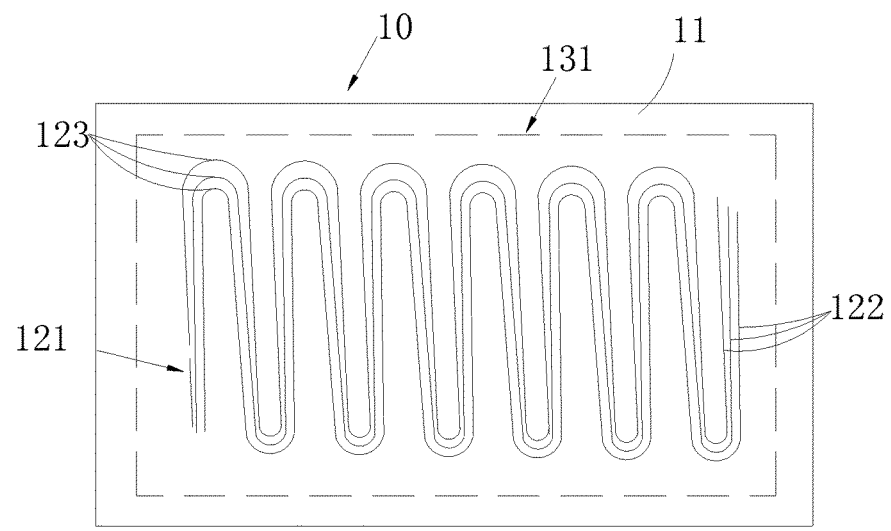
FIG. 4 is a top view of a first embodiment of the arrangement of the diameters of the bending portions of the cablings of the optical fiber rows of the optical fiber sensing layer provided by the embodiment of the application.

As shown in FIG. 3 and FIG. 4, the diameters of the bending portions 123 of the cablings 121 of the same optical fiber row 122 on the same interlayer 13 are equal. In this way, the diameters of the bending portions 123 are equal and changes regularly, which helps the arrangement of the cablings 121 of the same optical fiber row 122; the bending portions 123 of the cablings 121 of different optical fiber rows 122 on the same interlayer 13 are increased or decreased gradually along the second direction, since the optical fiber rows 122 having bending portions 123 with small diameters fill and table in the optical fiber rows 122 having bending portions 123 with large diameters gradually, in this embodiment, the diameters of the bending portions 123 of the cablings 121 of the optical fiber row 122 on the pressure-sensitive assembly film 11 will appear a gradually increasing or decreasing transitional trend, which makes the cablings 121 of the optical fiber row 122 on the pressure-sensitive assembly film 11 be more regular and denser.

Similarly, it enables the optical fiber sensing area 131 on the pressure-sensitive assembly film 11 to sense the compression on the pressure-sensitive assembly film 11 more sensitively, thus the variation of the luminance decay signal can be captured more sensitively and precisely. Therefore, the sensitivity of the aforesaid optical fiber sensing layer 10 is uniform, the luminance decay value of the aforesaid optical fiber sensing layer 10 is relative consistent, the sensitivity of the aforesaid optical fiber sensing layer 10 is high and can be adjusted, and the resolution of the aforesaid optical fiber sensing layer 10 is high.

The following embodiment is a second embodiment of the diameter arrangement of the bending portion 123 of the cabling 121 of the optical fiber row 122.

Figure 5:
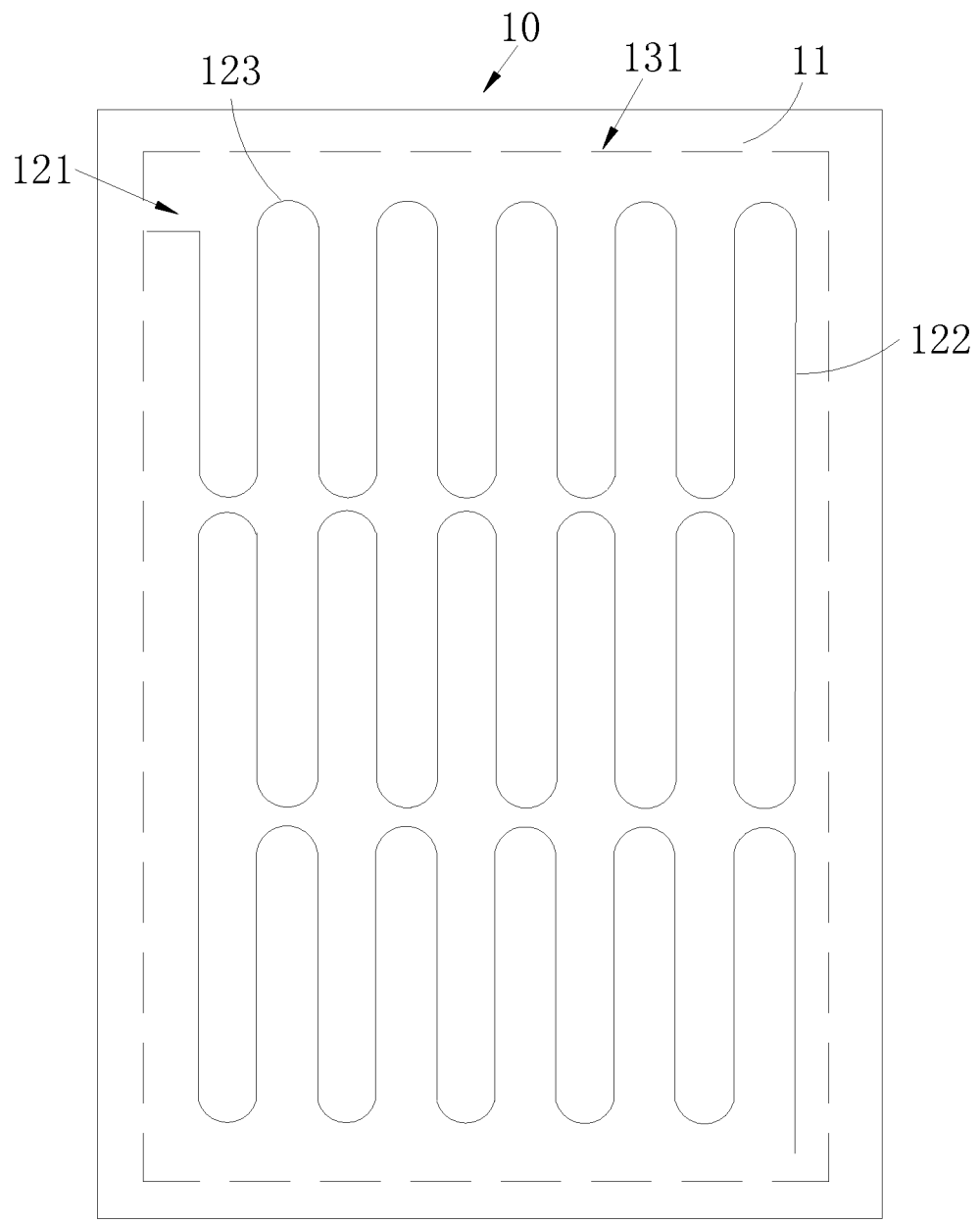
FIG. 5 is a top view of a second embodiment of the arrangement of the diameters of the bending portions of the cablings of the optical fiber rows of the optical fiber sensing layer provided by the embodiment of the application.

As shown in FIG. 3 and FIG. 5, the diameters of the bending portions 123 of the cablings 121 of all the optical fiber rows 122 on the same interlayer are equal. In this way, the diameters of the bending portions 123 of all the optical fiber rows 122 are equal and changes regularly, which helps the path of the optical fiber row 122 distribute regularly, uniformly, densely on the pressure-sensitive assembly film 11. Similarly, the sensitivity of the aforesaid optical fiber sensing layer 10 is uniform, the luminance decay value of the aforesaid optical fiber sensing layer 10 is relative consistent, the sensitivity of the aforesaid optical fiber sensing layer 10 is high and can be adjusted, and the resolution of the aforesaid optical fiber sensing layer 10 is high.

The following embodiment is a third embodiment of the diameter arrangement of the bending portion 123 of the cabling 121 of the optical fiber row 122.

Figure 6:
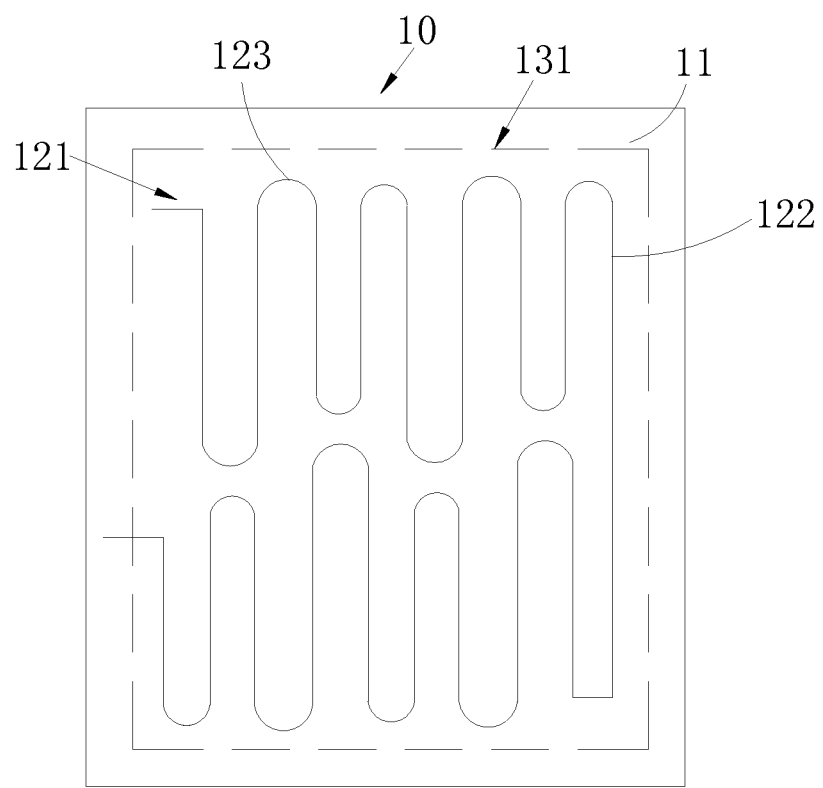
FIG. 6 is a top view of a third embodiment of the arrangement of the diameters of the bending portions of the cablings of the optical fiber rows of the optical fiber sensing layer provided by the embodiment of the application.

As shown in FIG. 3 and FIG. 6, the diameters of the bending portions 123 of the cablings 121 of the same optical fiber row 122 on the same interlayer are not equal, and every two adjacent optical fiber rows 122 are centrosymmetrical. In this way, every two optical fiber rows 122 become a group of segments, and many groups of segments are parallel and distributed on the pressure-sensitive assembly film 11. Similarly, the regular changes of the cablings 121 of the optical fiber rows 122 helps the sensitivity of the aforesaid optical fiber sensing layer 10 be uniform, the luminance decay value of the aforesaid optical fiber sensing layer 10 be relative consistent, the sensitivity of the aforesaid optical fiber sensing layer 10 be high and can be adjusted, and the resolution of the aforesaid optical fiber sensing layer 10 be high.

The following embodiment is a fourth embodiment of the diameter arrangement of the bending portion 123 of the cabling 121 of the optical fiber row 122.

Figure 7:
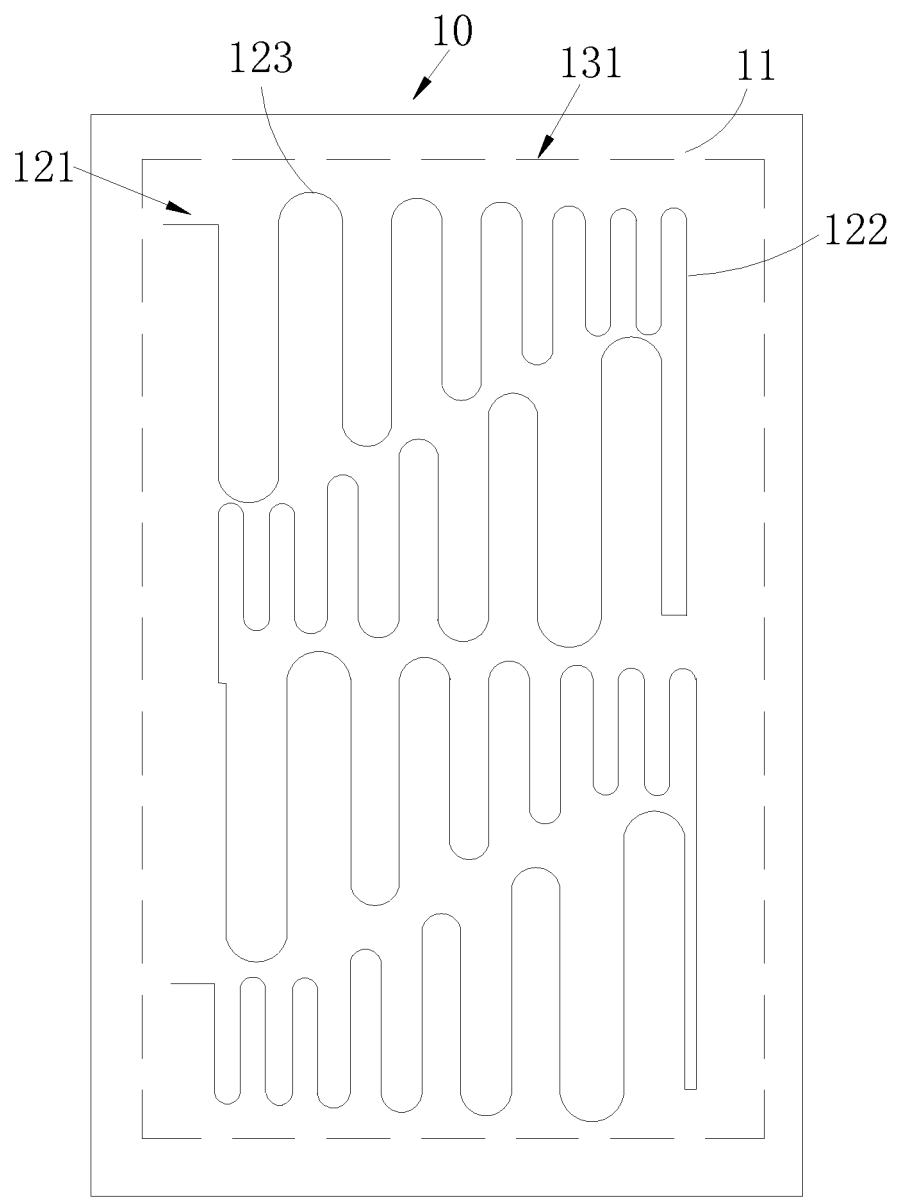
FIG. 7 is a top view of a fourth embodiment of the arrangement of the diameters of the bending portions of the cablings of the optical fiber rows of the optical fiber sensing layer provided by the embodiment of the application.

As shown in FIG. 3 and FIG. 7, as an optimization of the third embodiment, the diameters of the bending portions 123 of the cablings 121 of the same optical fiber row 122 on the same interlayer are increased or decreased gradually along the first direction. In this way, in the cablings 121 of two adjacent optical fiber rows 122, there is a large diameter end of one optical fiber row 122 and a small diameter end of another optical fiber row 122. The large diameter end fills the space vacated by the small diameter end of another optical fiber row 122. The cablings 121 of the two adjacent optical fiber rows 122 compensate the vacant space mutually. Therefore, such cablings 121 can utilize the space on the pressure-sensitive assembly film 11 fully, and the cablings 121 of the optical fiber row 122 can distribute more densely. Similarly, the sensitivity of the aforesaid optical fiber sensing layer 10 is uniform, the luminance decay value of the aforesaid optical fiber sensing layer 10 is relative consistent, the sensitivity of the aforesaid optical fiber sensing layer 10 is high and can be adjusted, and the resolution of the aforesaid optical fiber sensing layer 10 is high.

The embodiment is a first embodiment of the arrangement of the cablings 121 of the optical fiber row 122 on every interlayer 13.

Figure 8:
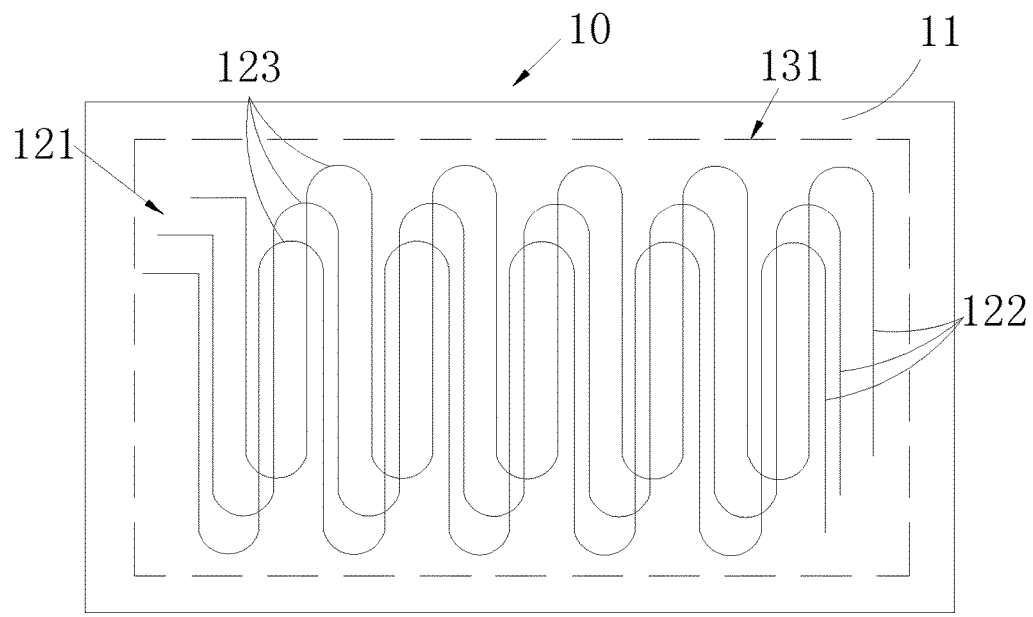
FIG. 8 is another top view of a first embodiment of the arrangement of the cablings of the optical fiber rows on each interlayer of the optical fiber sensing layer provided by the embodiment of the application.

As shown in FIG. 3 and FIG. 8, with respect to the arrangement of the diameters of the bending portions 123 of the cablings 121 of the optical fiber row 122, no matter which one of the aforesaid four arrangements is used, the patterns formed by the cablings 121 of the optical fiber row 122 on every interlayer 13 are consistent, and the bending portions 123 of the cablings 121 of every optical fiber row 122 on every two adjacent interlayers 13 stagger the same distance along the first direction. Because the shape of every optical fiber row 122 is an S-shape, the paths of the optical fiber rows 122 on both sides of every bending portion 123 are parallel with each other, the distance between the paths of the optical fiber rows 122 on both sides of the bending portion 123 is not less than the minimum diameter of the bending portion 123. Therefore, the paths of the bilateral optical fiber rows 122 have a certain distance along the first direction, and the bending portions 123 of the cablings 121 of the two layers of vertically adjacent optical fiber rows 122 stagger the same distance along the first direction, so as to make the paths of the optical fiber rows 122 at opposite sides of the bending portion 123 of other layers just fit into the interval between the paths of the optical fiber rows 122 at opposite sides of a bending portion 123 of a lower layer. In this way, the blind area caused by the large interval is avoided. On the contrary, because the compression of the pressure-sensitive assembly film 11 in the interval is sensed by the circuit of optical fiber row 122 of the upper layer so as to help the optical fiber sensing area 131 of the pressure-sensitive assembly film 11 sense the compression of the pressure-sensitive assembly film 11 more sensitively, the variation of the luminance decay signal can be captured more sensitively and precisely. This helps the sensitivity of the aforesaid optical fiber sensing layer 10 be uniform, the luminance decay value of the aforesaid optical fiber sensing layer 10 be relative consistent, the sensitivity of the aforesaid optical fiber sensing layer 10 be high and can be adjusted, and the resolution of the aforesaid optical fiber sensing layer 10 be high.

Moreover, piling up the paths of the bilateral optical fiber rows 122 at opposite sides of the bending portion 123 of an upper layer in the interval between the paths of the optical fiber rows 122 of at opposite sides of the bending portion 123 of a lower layer helps the thickness of the of the aforesaid optical fiber sensing layer 10 be decreased vertically, so that the optical fiber sensing layer 10 can be thinner and smaller.

The following embodiment is a second embodiment of the arrangement of the cablings 121 of the optical fiber row 122 on every interlayer 13.

Figure 9:
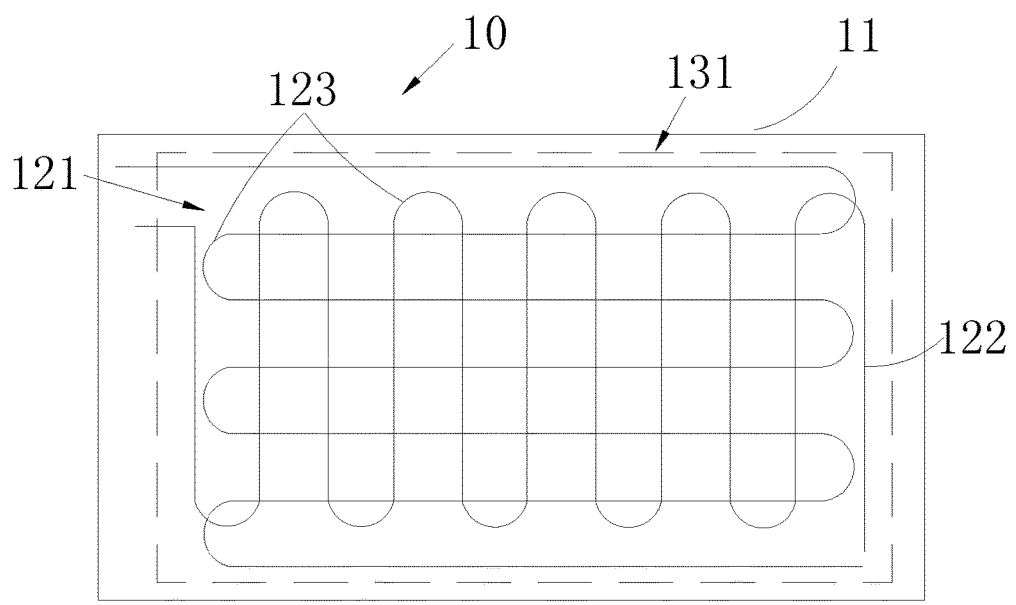
FIG. 9 is a top view of a second embodiment of the arrangement of the cablings of the optical fiber rows on each interlayer of the optical fiber sensing layer provided by the embodiment of the application.
Figure 10:
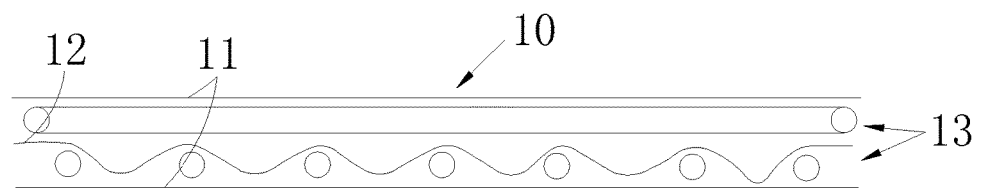
FIG. 10 is a cutaway view of the optical fiber sensing layer provided by FIG. 9.

As shown in FIG. 9 and FIG. 10, certainly, with respect to the diameter arrangement of the bending portions 123 of the cablings 121 of the optical fiber row 122, no matter which one of the aforesaid four arrangements is used, the cablings 121 of the optical fiber rows 122 on two adjacent interlayers 13 are arranged to stagger horizontally and longitudinally. In this way, the cablings 121 of the upper and lower layer optical fiber rows 122 pile up as a grid shape vertically. Therefore, a grip-like optical fiber sensing area 131 will be formed on the pressure-sensitive assembly film 11. Similarly, the cablings 121 of the optical fiber row 122 are arranged on the pressure-sensitive assembly film 11 uniformly and regularly. This helps the sensitivity of the aforesaid optical fiber sensing layer 10 be uniform, the luminance decay value of the aforesaid optical fiber sensing layer 10 be relative consistent, the sensitivity of the aforesaid optical fiber sensing layer 10 be high and can be adjusted, and the resolution of the aforesaid optical fiber sensing layer 10 be high.

Figure 12:
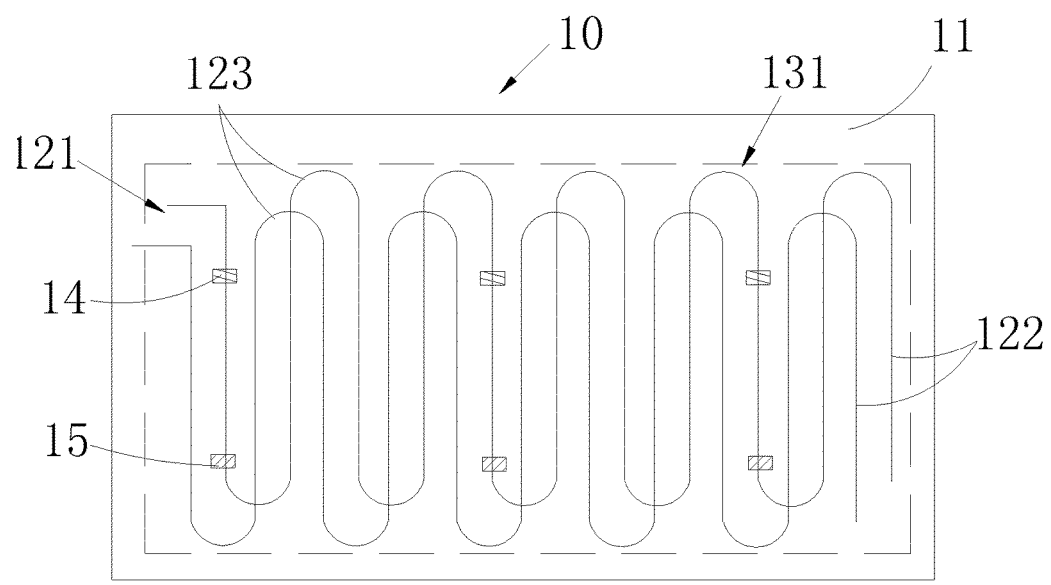
FIG. 12 is a top view of the optical fiber sensing layer which includes temperature sensing units and moisture sensing units provided by the embodiment of the application.

As shown in FIG. 3 and FIG. 12, this embodiment is a detailed embodiment about an optical fiber sensing layer 10 which is configured for detecting temperature and moisture. A temperature sensing unit 14 and a moisture sensing unit 15 can be arranged in an interlayer 13 separately or simultaneously. The temperature sensing unit 14 and moisture sensing unit 15 are arranged to surround the optical fiber row 122. In this way, when the temperature sensing unit 14 expands because of being heated, or when the moisture sensing unit 15 expands because of moisture absorption, the temperature sensing unit 14 and the moisture sensing unit 15 will squeeze the optical fiber row 122 and make the optical fiber row 122 deform, then the luminance decay value will be changed. Therefore, the aforesaid optical sensing layer 10 can be used for displaying the temperature and moisture of urine.

Figure 11:
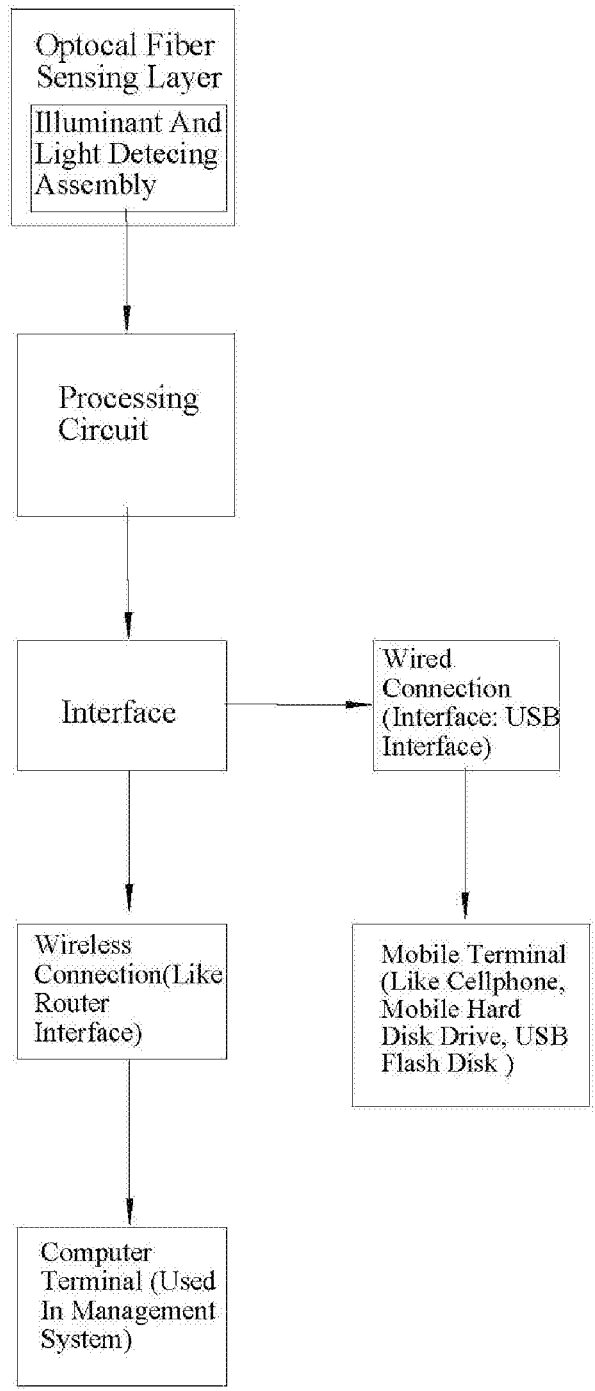
FIG. 11 is a work flow chart of a monitoring system provided by another object of an embodiment of the application.

As shown in FIG. 11, the embodiment further provides a monitoring system, comprising the aforesaid optical fiber sensing layer, an illuminant configured to provide light to the optical fiber sensing layer 10, an light detecting assembly configured to detect the luminance decay signal transmitted from the optical fiber sensing layer, a processing circuit configured to transform the luminance decay signal transmitted from the light detecting assembly into data representing human physiological activities, and an interface electrically connected with the processing circuit and configured to transmit the data to a user terminal.

It should be noted that, the user terminal includes a mobile terminal and a computer terminal. The mobile terminal includes a cellphone, a mobile hard disk drive, a USD flash disk, a storage card, etc. Accordingly, the interface includes a USB interface which can be connected with the mobile terminal, a storage card interface, a router interface which can be communicated with the computer terminal through Internet, etc.

Since the optical fiber sensing layer is adopted in the aforesaid monitoring system, the optical fiber sensing layer can sense the compression on the pressure-sensitive assembly film 11 quickly and precisely, capture the changes of the luminance decay signal more sensitively and precisely, and transmit the variation of the luminance decay signal to the processing circuit. Afterwards, the variation of the luminance decay signal is transmitted to the processing circuit by the light detecting assembly. The processing circuit transforms the luminance decay signal into data representing human physiological activities in time. Finally, the processing circuit communicates with a mobile terminal or a computer terminal through a USB interface, a storage card interface or a router interface to output the data representing the human physiological activities. For example, if the data is transmitted to a cellphone, the user can monitor his/her physiological activities data conveniently and momentarily. If the data is transmitted to a computer, the management system in the computer can batch and monitor a large amount of users' physiological activities data. All in all, the aforesaid monitoring system can detect human's and animal's physiological activities such as breaths, heartbeats, sleeps, temperatures, etc., and moisture quickly and precisely. The monitoring system has characteristics of a high and adjustable sensitivity, a high resolution, an electromagnetic interference resistance, and a uniform sensitivity.

The foregoings are merely the preferred embodiments of the present application, and are not intended to limit the present application, any modification, equivalent replacement, improvement, etc, made within the spirit and principle of the present application, should be encompassed in the scope of the present application.

What is claimed is:

1. An optical fiber sensing layer, comprising:
   two layers of pressure-sensitive assembly films which are vertically superposed and flexible; and
   at least one layer of flexible and smooth film which vertically separates a space between the two layers of pressure-sensitive assembly films into at least two interlayers, each interlayer is provided with at least one optical fiber row which extends along a first direction and has several S-shaped concatenated cablings, a bending portion of each cabling of the optical fiber row of the two vertically adjacent interlayers are staggered and superposed,
   wherein a luminance decay signal is generated when at least one of the optical fiber rows deforms axially, and
   an area on the pressure-sensitive assembly where the optical fiber rows are arranged forms an optical fiber sensing area, mechanical deformation of the optical fiber rows of the optical fiber sensing area and the pressure-sensitive assembly film are reflected by measuring the luminance decay signal generated by the optical fiber rows.

2. The optical fiber sensing layer according to claim 1, wherein, the number of the optical fiber rows on each interlayer is at least two, the at least two optical fiber rows in each interlayer are arranged to be parallel along a second direction perpendicular to the first direction, and two adjacent optical fiber rows are end to end.

3. The optical fiber sensing layer according to claim 2, wherein, the diameters of the bending portions of the cablings of the same optical fiber row on the same interlayer are equal, the diameters of the bending portions of the cablings of different optical fiber rows on the same interlayer increase or decrease gradually along the second direction, the bending portions with a small diameter are arranged in the bending portions with a large diameter.

4. The optical fiber sensing layer according to claim 3, wherein,
   patterns formed by the cablings of all the optical fiber rows on each interlayer are consistent, and the bending portions of the cablings of each optical fiber row on two adjacent interlayers stagger the same distance along the first direction, and
   paths of the optical fiber rows on both sides of each of the bending portions are parallel to each other, a distance between the paths of the optical fiber rows on both sides of each of the bending portions is not less than the minimum diameter of said bending portion, the paths of the optical fiber rows in a first one of the interlayers are arranged in intervals between the paths of the optical fiber rows in a second one of the interlayers.

5. The optical fiber sensing layer according to claim 3, wherein, the cablings of the optical fiber rows on two adjacent interlayers are arranged to stagger transversely and longitudinally, the cablings of the layer optical fiber rows in the two adjacent interlayers form a grid shape when viewed vertically.

6. The optical fiber sensing layer according to claim 2, wherein, the diameters of the bending portions of the cablings of all the optical fiber rows on the same interlayer are equal.

7. The optical fiber sensing layer according to claim 6, wherein,
   patterns formed by the cablings of all the optical fiber rows on each interlayer are consistent, and the bending portions of the cablings of each optical fiber row on two adjacent interlayers stagger the same distance along the first direction, and
   paths of the optical fiber rows on both sides of each of the bending portions are parallel to each other, a distance between the paths of the optical fiber rows on both sides of each of the bending portions is not less than the minimum diameter of said bending portion, the paths of the optical fiber rows in a first one of the interlayers are arranged in intervals between the paths of the optical fiber rows in a second one of the interlayers.

8. The optical fiber sensing layer according to claim 6, wherein, the cablings of the optical fiber rows on two adjacent interlayers are arranged to stagger transversely and longitudinally, the cablings of the layer optical fiber rows in the two adjacent interlayers form a grid shape when viewed vertically.

9. The optical fiber sensing layer according to claim 2, wherein, the diameters of the bending portions of the cablings of the same optical fiber row on the same interlayer are unequal, and two adjacent optical fiber rows are centrosymmetrical.

10. The optical fiber sensing layer according to claim 9, wherein, the diameters of the bending portions of the cablings of the same optical fiber row on the same interlayer increases or decreases gradually along the first direction.

11. The optical fiber sensing layer according to claim 10, wherein,
    patterns formed by the cablings of all the optical fiber rows on each interlayer are consistent, and the bending portions of the cablings of each optical fiber row on two adjacent interlayers stagger the same distance along the first direction, and
    paths of the optical fiber rows on both sides of each of the bending portions are parallel to each other, a distance between the paths of the optical fiber rows on both sides of each of the bending portions is not less than the minimum diameter of said bending portion, the paths of the optical fiber rows in a first one of the interlayers are arranged in intervals between the paths of the optical fiber rows in a second one of the interlayers.

12. The optical fiber sensing layer according to claim 10, wherein, the cablings of the optical fiber rows on two adjacent interlayers are arranged to stagger transversely and longitudinally, the cablings of the layer optical fiber rows in the two adjacent interlayers form a grid shape when viewed vertically.

13. The optical fiber sensing layer according to claim 9, wherein,
    patterns formed by the cablings of all the optical fiber rows on each interlayer are consistent, and the bending portions of the cablings of each optical fiber row on two adjacent interlayers stagger the same distance along the first direction, and
    paths of the optical fiber rows on both sides of each of the bending portions are parallel to each other, a distance between the paths of the optical fiber rows on both sides of each of the bending portions is not less than the minimum diameter of said bending portion, the paths of the optical fiber rows in a first one of the interlayers are arranged in intervals between the paths of the optical fiber rows in a second one of the interlayers.

14. The optical fiber sensing layer according to claim 9, wherein, the cablings of the optical fiber rows on two adjacent interlayers are arranged to stagger transversely and longitudinally, the cablings of the layer optical fiber rows in the two adjacent interlayers form a grid shape when viewed vertically.

15. The optical fiber sensing layer according to claim 2, wherein, patterns formed by the cablings of all the optical fiber rows on each interlayer are consistent, and the bending portions of the cablings of each optical fiber row on two adjacent interlayers stagger the same distance along the first direction.

16. The optical fiber sensing layer according to claim 2, wherein, the cablings of the optical fiber rows on two adjacent interlayers are arranged to stagger transversely and longitudinally.

17. The optical fiber sensing layer according to claim 2, each of the bending portions has a radian of 180 degrees.

18. The optical fiber sensing layer according to claim 1, wherein, each of the bending portions of each cabling has a diameter of at least 10 mm.

19. The optical fiber sensing layer according to claim 1, wherein a temperature sensing unit and a moisture sensing unit are arranged, separately or simultaneously, in the interlayer, and the temperature sensing unit and the moisture sensing unit each surround one of the optical fiber rows.

20. The optical fiber sensing layer according to claim 1, wherein the pressure-sensitive assembly films are silica gel, textile fabric, or polyethylene film.

* * * * *